(12) United States Patent
Amtmann

(10) Patent No.: US 7,078,566 B2
(45) Date of Patent: Jul. 18, 2006

(54) SALTS OF GUANIDINE DERIVATIVES AND PHARMACEUTICAL PREPARATIONS CONSISTING THEREOF

(75) Inventor: Eberhard Amtmann, Heidelberg (DE)

(73) Assignee: Biosphinks Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/820,121

(22) Filed: Apr. 8, 2004

(65) Prior Publication Data

US 2004/0192717 A1    Sep. 30, 2004

Related U.S. Application Data

(63) Continuation-in-part of application No. PCT/EP02/11338, filed on Oct. 10, 2002.

(30) Foreign Application Priority Data

Oct. 10, 2001    (DE) ................ 101 49 919

(51) Int. Cl.
C07C 279/02    (2006.01)
A61K 31/155    (2006.01)

(52) U.S. Cl. .............. 564/230; 564/237; 564/238; 564/239; 564/240; 514/634

(58) Field of Classification Search .............. None
See application file for complete search history.

(56) References Cited

U.S. PATENT DOCUMENTS 3,740,338 A * 6/1973 Allphin ............ 252/77
3,915,918 A   10/1975 Springle et al.

FOREIGN PATENT DOCUMENTS

| DE | 1238896 | 4/1967 |
|---|---|---|
| DE | 1802394 | 5/1969 |
| DE | 286580 | 8/1984 |
| EP | 0188333 | 7/1986 |
| EP | 0315467 | 5/1989 |
| GB | 768089 | 2/1957 |
| GB | 842325 | 7/1960 |
| GB | 932951 | 7/1963 |
| GB | 950693 | 2/1964 |
| GB | 1091049 | 11/1967 |
| GB | 1257270 | 12/1971 |
| GB | 1475073 | 6/1977 |
| WO | WO 84/01490 | 4/1984 |

OTHER PUBLICATIONS

Chemical Abstract of Japanese Patent, JP 11035546, Feb. 9, 1999. vol. 130, Ref. 213456.
Chemical Abstract, "The Effect of some oligoamines and -guanidines on membrane permeability in higher plants", vol. 97, Ref. 124283.
Chemical Abstract, "Formation of salts by reaction of benzamidine with 2-bromo methyl alkenoates", vol. 85, Ref. 32586.

* cited by examiner

Primary Examiner—Brian Davis
(74) Attorney, Agent, or Firm—Gail C. Silver; Borden Ladner Gervais LLP

(57) ABSTRACT

This invention relates to salts of guanidine derivatives of formula R—X—C($=$NH)NH$_3^+$Z$^-$, wherein X represents a valence bond, —CH$_2$—NH—, —CH$_2$—NH—NH— or —CH$=$N—NH—; R represents a linear or branched C$_1$–C$_{30}$ alkyl, C$_3$–C$_{20}$ cycloalkyl, adamantyl, norbornyl, tricyclodecyl, benzyl, furyl, pyridyl, anthracyl, naphthyl, phenanthryl, perinaphthyl or quinuclidinyl residue, which can be substituted by one or more hydroxyl groups, C$_1$–C$_4$ alkoxy groups, C$_1$–C$_4$ alkyl groups and/or one or more halogen atoms or one or more amino groups; Z represents O—CO—Y, O—S(O)$_2$—Y, or O—P(O)(OH)—Y; and Y represents a linear or branched C$_1$–C$_{12}$ alkyl, C$_3$–C$_8$ cycloalkyl, benzyl, furyl or pyridyl residue, which can be substituted by one or more hydroxyl groups, carboxylic acid groups, C$_1$–C$_4$ alkoxy groups, C$_1$–C$_4$ alkyl groups and/or one or more halogen atoms or one or more amino groups. These compounds are useful for treating tumor diseases, autoimmune diseases, cardiovascular diseases, infections, and viral diseases.

15 Claims, 3 Drawing Sheets

SALTS OF GUANIDINE DERIVATIVES AND PHARMACEUTICAL PREPARATIONS CONSISTING THEREOF

CROSS REFERENCE TO RELATED APPLICATIONS

This application is a continuation-in-part of PCT/EP02/11338, filed on Oct. 10, 2002, claiming priority from German Patent Application No. 101 49 919.1 filed Oct. 10, 2001, both of which are incorporated by reference herein.

FIELD OF THE INVENTION

The invention relates to new salts of guanidine derivatives and pharmaceutical preparations containing these as the active ingredient, as well as their preparation.

BACKGROUND OF THE INVENTION

WO 97/45401, incorporated by reference herein, discloses guanidine derivatives of the general formula (1)

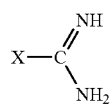

Formula 1 in which X represents the group, $-R^1$, $-NHR^1$, $-NH-NH-CHR^1R^2$ or $-NH-N=CR^1R^2$, whereby $R^1$ and $R^2$ independent of each other represent hydrogen, a linear or branched $C_3-C_{20}$ alkyl or $C_3-C_{20}$ cycloalkyl, adamantyl, norbornyl, tricyclodecyl or benzyl, pyridyl, indolyl, quinolyl, anthracyl, phenantryl, perinaphthyl or quinuclidinyl radical. The use of the compounds as active ingredient in pharmaceutical preparations is based mainly on the inhibition of sphingomyelinases. The free bases are described exclusively as examples of compounds according to formula 1.

Due to their detergent structure, the bases described and their salts obtained by neutralization with inorganic acids or by dissolution in buffered saline (physiological sodium chloride solution) possess strong hemolytic and tissue-damaging properties. Moreover, in the presence of inorganic phosphate ions, inorganic salts form phosphates of the guanidines which are insoluble in aqueous solutions. This causes them to be precipitated, and thereby rendered pharmaceutically inactive, in the blood at relatively low concentrations. For these reasons, the pharmaceutical utility of guanidine derivatives is strongly limited.

SUMMARY OF THE INVENTION

Thus, it is the object of the present invention to provide a physiologically tolerable and, at the same time, efficacious form of administration for the guanidine derivatives.

Surprisingly, it was found that salts formed by converting active guanidine derivatives with certain organic acids have up to 100-fold lower hemolytic activity and excellent local tolerability at unchanged efficacy, i.e. especially as it concerns the inhibition of sphingomyelinase. Moreover, these salts are not precipitated by inorganic phosphates. For this reason, the salts according to the invention possess a much wider dosing range.

Therefore, the task specified above is solved by salts of the general formula:

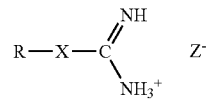

wherein

X represents a valence bond, $-CH_2-NH-$, $-CH_2-NH-NH-$ or $-CH=N-NH-$,

R represents a linear or branched $C_1-C_{30}$ alkyl, $C_3-C_{20}$ cycloalkyl, adamantyl, norbornyl, tricyclodecyl, benzyl, furyl, pyridyl, anthracyl, naphthyl, phenanthryl, perinaphthyl or quinuclidinyl residue, which can be substituted by one or more hydroxyl groups, $C_1-C_4$ alkoxy groups, $C_1-C_4$ alkyl groups and/or one or more halogen atoms or one or more amino groups, and Z represents $O-CO-Y$, $O-S(O)_2-Y$, or $O-P(O)(OH)-Y$, in which Y represents a linear or branched $C_1-C_{12}$ alkyl, $C_3-C_8$ cycloalkyl, benzyl, furyl or pyridyl residue, which can be substituted by one or more hydroxyl groups, carboxylic acid groups, $C_1-C_4$ alkoxy groups, $C_1-C_4$ alkyl groups and/or one or more halogen atoms or one or more amino groups.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
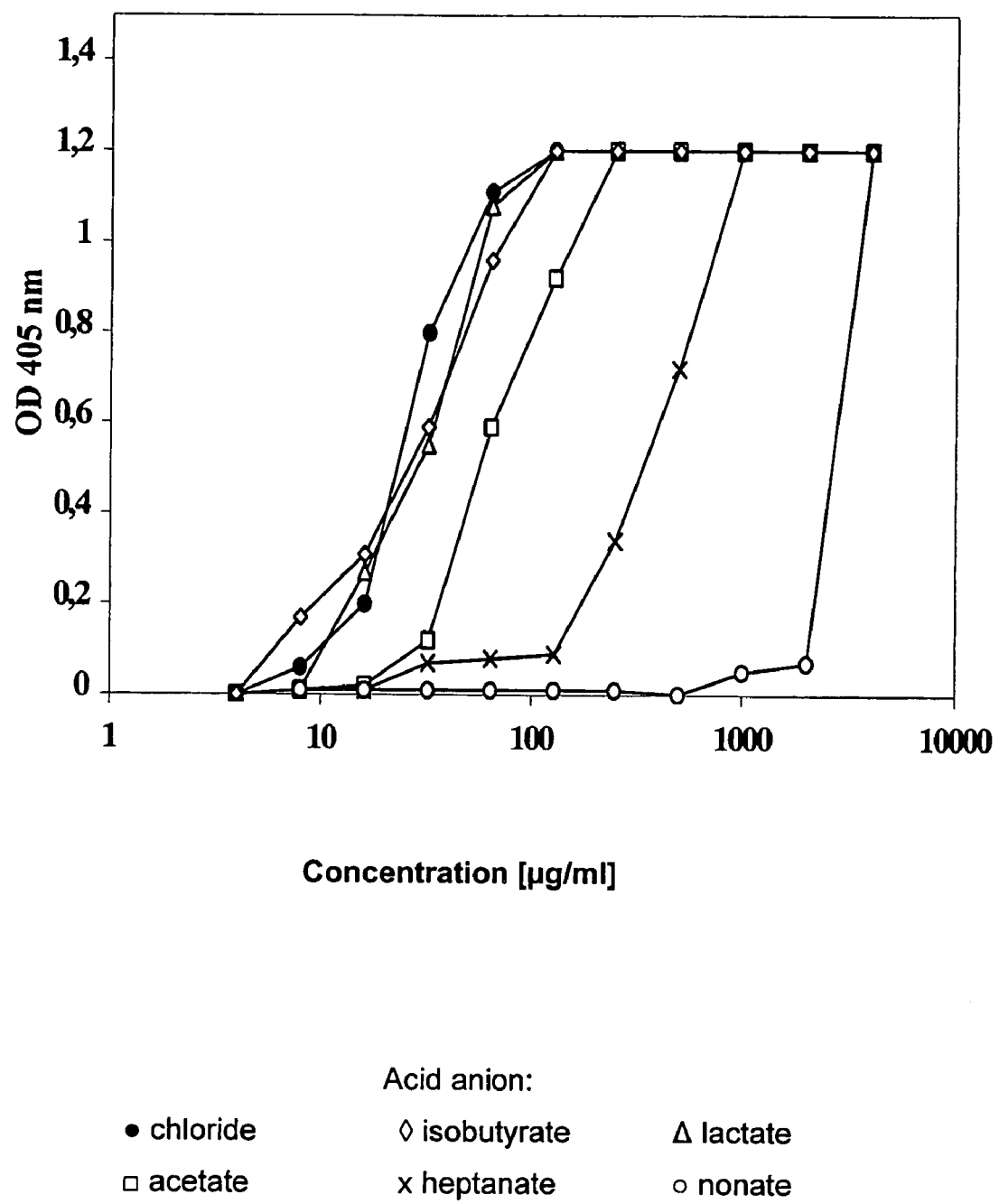
FIG. 1 is a graph showing optical density as a function of the logarithm of concentration for various guanidine salts.

This invention relates to salts of the general formula:

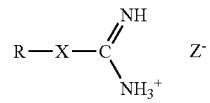

wherein

X represents a valence bond, $-CH_2-NH-$, $-CH_2-NH-NH-$ or $-CH=N-NH-$,

R represents a linear or branched $C_1-C_{30}$ alkyl, $C_3-C_{20}$ cycloalkyl, adamantyl, norbornyl, tricyclodecyl, benzyl, furyl, pyridyl, anthracyl, naphthyl, phenanthryl, perinaphthyl or quinuclidinyl residue, which can be substituted by one or more hydroxyl groups, $C_1-C_4$ alkoxy groups, $C_1-C_4$ alkyl groups and/or one or more halogen atoms or one or more amino groups, Z represents O—CO—Y, O—S(O)$_2$—Y, or O—P(O)(OH)—Y, in which Y represents a linear or branched C$_1$-C$_{12}$ alkyl, C$_3$-C$_8$ cycloalkyl, benzyl, furyl or pyridyl residue, which can be substituted by one or more hydroxyl groups, carboxylic acid groups, C$_1$-C$_4$ alkoxy groups, C$_1$-C$_4$ alkyl groups and/or one or more halogen atoms or one or more amino groups.

In one aspect, Z is O—C(O)—Y.

It is preferred for R to represent pentyl, hexyl, heptyl, octyl, nonyl, decyl, undecyl, dodecyl, tridecyl, cyclododecyl, tricyclo[5,2,1,0$^{2,6}$]-decyl, bicyclo[2,2,1]-cyclohexyl or toluyl. A decyl residue is particularly advantageous.

It is preferred for X to represent —CH$_2$—NH—NH— or —CH=N—NH—, with —CH=N—NH— being particularly preferred.

It is particularly advantageous for Y to represent methyl, ethyl, propyl, isopropyl, butyl, pentyl, hexyl, heptyl, octyl, nonyl, decyl, undecyl, and dodecyl as well as hydroxyethyl and 2-hydroxy-2,3-dicarboxylic acid propyl. Particularly preferred are methyl, ethyl, pentyl, heptyl, octyl, nonyl, decyl, undecyl, and dodecyl as well as hydroxyethyl and 2-hydroxy-2,3-dicarboxylic acid propyl.

Preferred compounds include salts of undecylaminoguanidine and undecylidineaminoguanidine, in particular salts in which Z is O—C(O)—Y, and Y represents a C$_{1-12}$ alkyl group (such as methyl, ethyl, propyl, isopropyl, butyl, pentyl, hexyl, heptyl, octyl, nonyl, decyl, undecyl, dodecyl), or where Y represents hydroxyethyl or 2-hydroxy-2,3-dicarboxylic acid propyl. Particularly preferred are such salts in which Y represents methyl, ethyl, pentyl, heptyl, octyl, nonyl, decyl, undecyl, dodecyl, hydroxyethyl, or 2-hydroxy-2,3-dicarboxylic acid propyl.

Particularly preferred compounds according to the present invention are undecylaminoguanidine acetate, undecylaminoguanidine lactate, undecylaminoguanidine oenanthate, undecylaminoguanidine pelargonate, undecylaminoguanidine hexanoate, undecylaminoguanidine octanoate, and undecylaminoguanidine decanoate; and, in particular, undecylideneaminoguanidine acetate, undecylideneaminoguanidine lactate, undecylideneaminoguanidine oenanthate (also known as undecylideneaminoguanidine heptanoate), undecylideneaminoguanidine pelargonate (also known as undecylideneaminoguanidine nonanoate), undecylideneaminoguanidine hexanoate, undecylideneaminoguanidine octanoate, and undecylideneaminoguanidine decanoate. Particularly advantageous is undecylideneaminoguanidine hexanoate.

In place of the carboxylic acids (i.e. Z=O—C(O)—Y), the correspondingly substituted sulfonic acids (i.e. Z=O—S(O)$_2$—Y) or phosphonic acids (Z=O—P(O)(OH)—Y) can be inserted.

It is self-evident that the present invention relates, as far as applicable, to the pure optical isomers and their mixtures as well as racemates, tautomers or stereoisomers.

The salts of guanidine derivatives according to the invention no longer possess a detergent effect, since the polar group of the guanidines is bound to a hydrophobic acid anion. This renders these compounds physiologically well-tolerated. Surprisingly, the guanidine salts according to the invention are soluble in water up to concentrations of 1,000 mmol/l and are not precipitated from the aqueous solution by phosphate ions. The efficacy, in contrast, in particular as it concerns the inhibition of sphingomyelinase, is not or not significantly affected. In some cases, the efficacy is increased.

The preparation of the guanidines is known, for instance from WO 97/45401, incorporated by reference herein. The guanidine salts according to the invention are simple to prepare by contacting the free bases with the corresponding free acids. This can be done in suitable solvents, mainly water, as well as without solvents, especially if the acid and/or the base is a liquid. It can be advantageous to add an excess of the acid.

The present invention also relates to pharmaceutical preparations containing the salts of the guanidine derivatives according to the invention as active ingredient. The pharmaceutical preparations can be used for the treatment of tumor diseases, autoimmune diseases, cardiovascular diseases, infections, and, in particular, viral diseases. The active ingredients are also suitable for prophylaxis. Preferred active ingredients are: undecylideneaminoguanidine acetate, undecylideneaminoguanidine lactate, and, in particular, undecylideneaminoguanidine oenanthate, undecylideneaminoguanidine pelargonate, and undecylideneaminoguanidine hexanoate, undecylideneaminoguanidine octanoate, and undecylideneaminoguanidine decanoate. Particularly advantageous is undecylideneaminoguanidine hexanoate.

Aside from the active ingredient according to the invention, the preparations according to the invention commonly contain excipients and additives facilitating the formulation into forms of administration. Moreover, for instance for combination preparations, other active ingredients can be added provided they are chemically compatible with the active ingredients according to the invention. The following forms of administration are considered: liquid preparations for injection; tablets, capsules, powders, solutions, suspensions or elixirs for oral application; ointments, creams, emulsions or lotions for topical application; powders and solutions for inhalation; and suppositories.

The methods for the preparation of forms of administration are known to a person skilled in the art. Aside from processing the salts according to the invention to the forms of administration, these active ingredients can also be processed to forms of administration by providing the free base and acid, preferably in equimolar amounts, and processing this mixture, if applicable, in the presence of additional excipients and additives. Thereby, the salt is formed either in situ or upon release from the form of administration in the body. Usable concentrations are in the range from 0.5 to 30% active ingredient in injection solutions and at least 1% active ingredient in preparations for the remaining forms of administration. The daily adult dose is between 5 and 1,000 mg.

In one aspect, the present invention provides a method for the treatment of tumor diseases, autoimmune diseases, cardiovascular diseases, infections or viral diseases comprising administering to a patient a pharmaceutically effective amount of the guanidinium salt in accordance with the invention.

The following examples are presented to further illustrate the present invention without limiting it to the examples presented.

EXAMPLE 1

Preparation of Undecylideneaminoguanidine Acetate

A total of 23.4 g (0.1 mol) undecylideneaminoguanidine (i.e. C$_{10}$H$_{21}$—CH=N—NH—C(NH)—NH$_2$, hereinafter abbreviated as C11AG) are slurried in 234 ml distilled water, heated to 60° C., and then 6.005 g glacial acetic acid are added slowly under stirring. After stirring for 30 minutes, the sample is filtered, and chilled to 0° C. The crystallized salt is removed by filtration and washed with ice-cold water. A total of 27.8 g of the acetate are obtained (yield 94.5%).

EXAMPLE 2

Preparation of Undecylideneaminoguanidine Oenanthate

A total of 23.4 g (0.1 mol) undecylideneaminoguanidine (C11AG) are slurried in 234 ml distilled water, heated to 60° C., and then 13.02 g oenanthic acid are added slowly under stirring. After stirring for 30 minutes, the sample is filtered, and chilled to 0° C. The crystallized salt is removed by filtration and washed with ice-cold water. A total of 22 g of the oenanthate are obtained (yield 60.4%).

EXAMPLE 3

Preparation of Undecylideneaminoguanidine Pelargonate

A total of 23.4 g (0.1 mol) undecylideneaminoguanidine (C11AG) are slurried in 234 ml distilled water, heated to 60° C., and then 15.82 g of pelargonic acid are added slowly under stirring. After stirring for 30 minutes, the sample is filtered, and chilled to 0° C. The crystallized salt is removed by filtration and washed with ice-cold water. A total of 36.1 g of the pelargonate are obtained (yield 92%).

EXAMPLE 4

Preparation of Additional Undecylideneaminoguanidine Salts

A total of 1.1 mmol acid and 1 mmol C11AG (234 mg) were dissolved in 3 ml ethylacetate. The excess of acid was removed by extracting thrice with distilled water. After drying in a vacuum, the salt was obtained with the yield being in excess of 90%. Table 1 shows an overview of the solubilities of the salts thus obtained as well as their melting points and the corresponding data of the salts from examples 1–3.

TABLE 1

| Acid anion | Solubility in water | Melting point |
| --- | --- | --- |
| Acetate | >10 mg/ml | 90° C. |
| Lactate | >10 mg/ml | 16° C. |
| Isobutyrate | >10 mg/ml | <4° C. |
| Heptanate | >10 mg/ml | 89° C. |
| Nonate | >10 mg/ml | 82° C. |
| Decanate | 1 mg/ml | 48° C. |
| Undecanate | 0.1 mg/ml | 81° C. |
| Dodecanate | 0.01 mg/ml | 68° C. |
| Dodecylphosphonate | 0.1 mg/ml | 78° C. |
| Undecylenate | 0.1 mg/ml | 62° C. |
| Chloride | >10 mg/ml | 63° C. |
| Palmitate | 0.01 mg/ml | 72° C. |
| Stearate | 0.01 mg/ml | 81° C. |

It is evident that even relatively long-chained acids provide salts that are relatively readily water-soluble. However, the not so readily water-soluble salts can in individual cases be more suitable for specific applications

EXAMPLE 5

Hemolytic Activity of Various C11AG Salts

The salts of lactic acid, acetic acid, hydrochloric acid, oenanthic acid, and pelargonic acid were prepared as described above. Mouse blood (obtained from the tail vein) was diluted 1:100 in isotonic glucose solution. The various C11AG salts were added to 0.1 ml aliquots of diluted mouse blood each at final concentrations of 4–4,000 µg/ml. After mixing and incubating at room temperature for 20 minutes, the samples were briefly centrifuged and the optical density at 405 nm was measured. The optical density is a measure of the quantity of hemoglobin released from the erythrocytes. FIG. 1 shows the optical density readings as a function of the logarithm of the concentration of the guanidine derivative. The final concentration increases by a factor of two from each measuring point to the next. It is evident that the guanidine derivatives according to the invention show substantial hemolytic activity only at concentrations of 32 µg/ml and above, whereas the chloride shows marked hemolytic activity already between 8 and 16 µg/ml.

EXAMPLE 6

Solubility of C11AG Salts in Phosphate Buffer

A 1 M potassium phosphate buffer solution, pH 7.4, was prepared. The salts of lactic acid, acetic acid, hydrochloric acid, oenanthic acid, and pelargonic acid, were added to a dilution series containing between 1,000 mM and 1 mM phosphate to establish a final concentration of the C11AG salt of 4 mM. The formation of crystals was monitored by microscope at 40-fold magnification. The results are shown in Table 2. While the chloride forms insoluble phosphates at concentrations as low as 1 mM, the acetate and the lactate precipitate only at a phosphate concentration of 10 mM and the oenanthate and the pelargonate are stable even in solutions containing 1,000 mM phosphate ions.

TABLE 2

| Salt | Concentration | Crystals |
| --- | --- | --- |
| Chloride | 1 mM–1,000 mM | yes |
| Acetate | 1 mM | no |
| Acetate | 10 mM–1,000 mM | yes |
| Lactate | 1 mM | no |
| Lactate | 10 mM–1,000 mM | yes |
| Oenanthate | 1 mM–1,000 mM | no |
| Pelargonate | 1 mM–1,000 mM | no |

EXAMPLE 7

Inhibition of Neutral Sphingomyelinase

The salts of lactic acid, acetic acid, hydrochloric acid, oenanthic acid, and pelargonic acid, were prepared as described above or in an analogous fashion. Paranitrophenylphosphoryl-choline was dissolved to a final concentration of 1 mg/ml in 0.1 M Tris at pH 7.2 and 10 mM $Mg_2Cl_2$. After adding 0.1 unit of neutral sphingomyelinase from Bacillus cereus, the various C11AG salts were added at concentrations between 0.1 and 1,000 µg/ml. After incubation at 37° C. for 24 h, the optical density at 405 nm was measured. The optical density is a measure for the quantity of cleaved substrate. Dose-effect curves were used to determine the concentration at which the enzyme activity is inhibited by 50% (IC50). The results are listed in Table 3. It is evident that the efficacy is even improved in some cases, but definitely in none of the cases is reduced significantly below the efficacy of the chloride.

TABLE 3

| Salt | IC50 [µg/ml] |
|---|---|
| Chloride | 0.8 |
| Acetate | 0.85 |
| Lactate | 0.9 |
| Oenanthate | 0.75 |
| Pelargonate | 0.95 |

EXAMPLE 8

Physiological Tolerability of Various C11AG Salts

The salts of acetic acid, hydrochloric acid, oenanthic acid, and pelargonic acid were used to prepare solutions in isotonic glucose solution at concentrations of 4 mM, 20 mM, 40 mM, and 120 mM. Aliquots of 0.1 ml each were administered to 3 nude mice (strain: Swiss, Nu/Nu) by subcutaneous application. After 24 h, the degree of tissue damage was recorded. The results are shown in Table 4, in which no visible damage=–, reddening=+, edemas=++, and necroses=+++. It is evident that the chloride leads to reddening and edemas at concentrations as low as 20 mM. The acetate is well-tolerated up to 20 mM and only at 120 mM shows the same degree of damage that was observed with 20 mM of the chloride. The preferred oenanthates and pelargonates show no damage whatsoever even at 120 mM.

TABLE 4

| Salt | Concentration | Finding |
|---|---|---|
| Chloride | 4 mM | 1 × +, 2 × – |
| Chloride | 20 mM | 1 × +, 2 × ++ |
| Chloride | 40 mM | 2 × ++, 1 × +++ |
| Chloride | 120 mM | 3 × +++ |
| Acetate | 4 mM–20 mM | 3 × – |
| Acetate | 120 mM | 1 × +, 2 × ++ |
| Oenanthate | 4 mM–120 mM | 3 × – |
| Pelargonate | 4 mM–120 mM | 3 × – |

EXAMPLE 9

Induction of Colitis and Treatment of Animals

Undecylideneaminoguanidine hexanoate was prepared as described in Example 4 or in an analogous manner.

Figure 2:
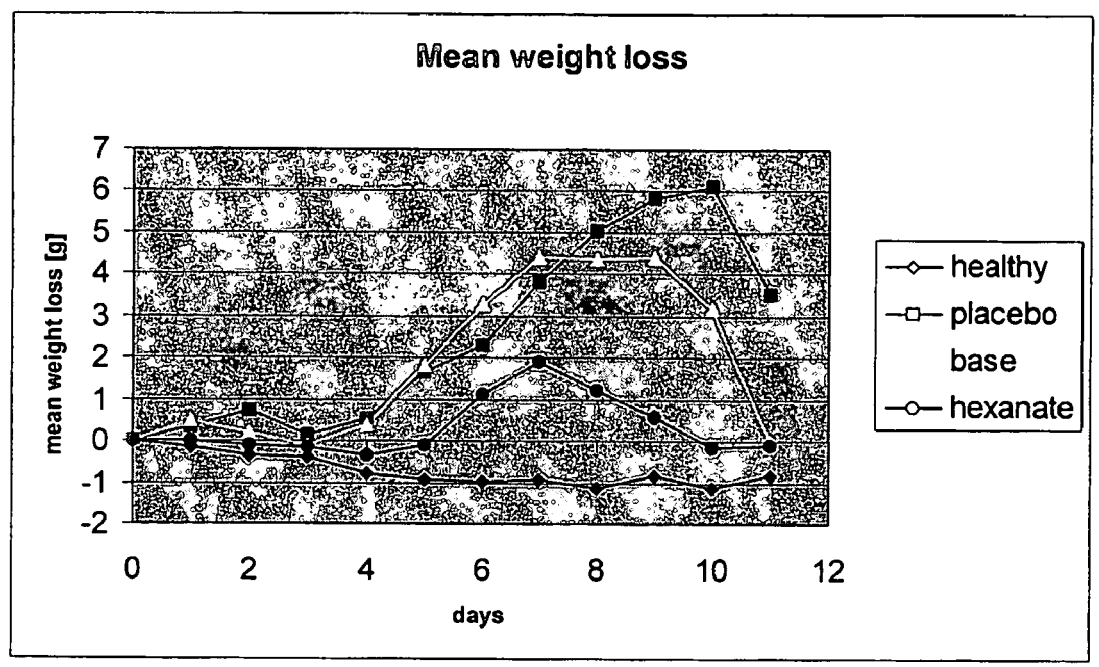
FIG. 2 is a is a graph showing mean weight loss as a function of time for mice under various conditions.

Female mice (strain Balb C, 9 weeks old) were obtained from Charles River and were kept under specific pathogen free conditions under an artificial day/night rhythm. Animals were fed with Altromin standard diet and received water ad libitum. Colitis was induced by addition of dextran sulfate (DSS) (MW 36,000–50,000, ICN, Aurora, Ohio, lot 2387F) to drinking water at a concentration of 7.5%. For C11AG treatment the free base of C11AG (lot 2-3-3) was used. Animals received Altromin powder food, mixed with 0.5 mg C11AG/g or with equimolar concentration of C11AG salt (i.e. 0.785 mg/g C11AG hexanate). As determined in calibration experiments Balb C mice (8–12 weeks old) consume each day 150 g food/kg body weight. The corresponding daily doses of C11AG were therefore: 75 and mg/kg/day. Body weight loss is one of the most evident symptoms of DSS induced colitis. Mean body weight was determined every day for each group and the weight loss was calculated. The mean weight losses are shown in FIG. 2.

Protection from DSS induced weight loss is more pronounced with the hexanoic acid salt of C11AG as compared to the free base.

EXAMPLE 10

Body Weight Loss in Animals with Colitis

Undecylideneaminoguanidine hexanoate, octanoate, and decanoate salts were prepared as described in Example 4 or in an analogous manner.

Figure 3:
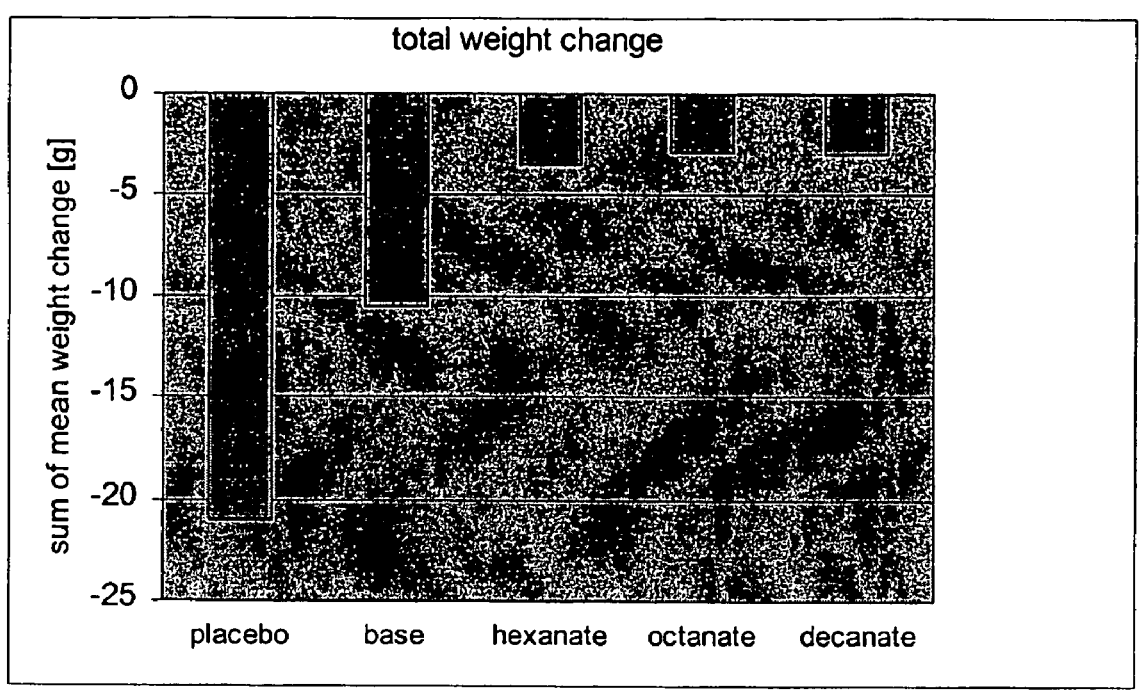
FIG. 3 is a graph showing mean weight loss for mice under various conditions.

Female mice (strain Balb C, 9 weeks old) were obtained from Charles River and were kept under specific pathogen free conditions under an artificial day/night rhythm. Animals were fed with Altromin standard diet and received water ad libitum.Colitis was induced by addition of dextran sulfate (DSS) (MW 36,000–50,000, ICN, Aurora, Ohio, lot 2387F) to drinking water at a concentration of 7.5%. For C11AG treatment the free base of C11AG (lot 2-3-3) was used. Animals received Altromin powder food, mixed with 0.5 mg C11AG/g or with equimolar concentration of C11AG salt (i.e. 0.785 mg/g C11AG hexanate, 0.855 mg/g C11AG octanate, 0.925 mg/g C11AG decanate). As determined in calibration experiments Balb C mice (8–12 weeks old) consume each day 150 g food/kg body weight. The corresponding daily doses of C11AG were therefore: 75 and mg/kg/day. Body weight loss is one of the most evident symptoms of DSS induced colitis. Mean body weight was determined every day for each group and the weight loss was calculated. Mean weight loss was added over a period of eleven days. The summarized mean weight losses are shown in FIG. 3.

Protection from DSS induced weight loss is more pronounced with the hexanoic, octanoic and decanoic acid salts of C11AG as compared to the free base.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A pharmaceutical preparation for the treatment of tumor diseases, autoimmune diseases, cardiovascular diseases, infections, or viral diseases, comprising one or more salts of guanidine derivatives corresponding to the formula

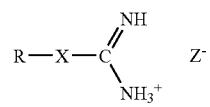

wherein
X represents —CH$_2$—NH—NH— or —CH=N—NH—,
R represents a linear or branched C$_1$–C$_{30}$ alkyl, C$_3$–C$_{20}$ cycloalkyl, or tricyclodecyl residue, which can be substituted by one or more hydroxyl groups, C$_1$–C$_4$ alkoxy groups, C$_1$–C$_4$ alkyl groups and/or one or more halogen atoms or one or more amino groups, and
Z represents O—CO—Y, O—S(O)$_2$—Y, or O—P(O)(OH)—Y, wherein Y represents a linear or branched $C_1$–$C_{12}$ alkyl, $C_3$–$C_8$ cycloalkyl, benzyl, furyl or pyridyl residue, which can be substituted by one or more hydroxyl groups, carboxylic acid groups, $C_1$–$C_4$ alkoxy groups, $C_1$–$C_4$ alkyl groups and/or one or more halogen atoms or one or more amino groups.

2. The preparation according to claim 1, wherein Z represents O—CO—Y.

3. The preparation according to claim 1, wherein R represents a pentyl, hexyl, heptyl, octyl, nonyl, decyl, undecyl, dodecyl, tridecyl, cyclododecyl, tricyclo[5,2,1,0$^{2,6}$]-decyl, or bicyclo[2,2,1]-heptyl residue.

4. The preparation according to claim 1, wherein R represents a decyl residue.

5. The preparation according to claim 1, wherein Y is methyl, ethyl, propyl, isopropyl, butyl, pentyl, hexyl, heptyl, octyl, nonyl, decyl, undecyl, dodecyl, hydroxyethyl or 2-hydroxy-2,3-dicarboxylic acid propyl.

6. The preparation according to claim 5, wherein R represents a decyl residue.

7. The preparation according to claim 1, said salt being undecylideneaminoguanidine acetate or undecylideneaminoguanidine lactate.

8. The preparation according to claim 1, said salt being undecylideneaminoguanidine oenanthate or undecylideneaminoguanidine pelargonate.

9. The preparation according to claim 1, said salt being undecylideneaminoguanidine decanoate.

10. The preparation according to claim 1, said salt being undecylideneaminoguanidine hexanoate.

11. The preparation according to claim 1, wherein Z is O—S(O)$_2$—Y (sulfonic acid group), or O—P(O)(OH)—Y (phosphonic acid group).

12. The preparation according to claim 1, further comprising a parmaceutically acceptable additives and/or excipients.

13. Method for the preparation of a pharmaceutical preparation for the treatment of tumor diseases, autoimmune diseases, cardiovascular diseases, infections, or viral diseases, comprising combining one or more salts of guanidine derivatives corresponding to the formula

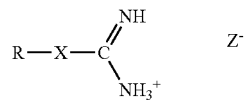

wherein

X represents —CH$_2$—NH—NH— or —CH=N—NH—,

R represents a linear or branched $C_1$–$C_{30}$ alkyl, $C_3$–$C_{20}$ cycloalkyl, or tricyclodecyl residue, which can be substituted by one or more hydroxyl groups, $C_1$–$C_4$ alkoxy groups, $C_1$–$C_4$ alkyl groups and/or one or more halogen atoms or one or more amino groups, and Z represents O—CO—Y, O—S(O)$_2$—Y, or O—P(O)(OH)—Y, wherein Y represents a linear or branched $C_1$–$C_{12}$ alkyl, $C_3$–$C_8$ cycloalky, benzyl, furyl or pyridyl residue, which can be substituted by one or more hydroxyl groups, carboxylic acid groups, $C_1$–$C_4$ alkoxy groups, $C_1$–$C_4$alky groups and/or one or more halogen atoms or one or more amino groups, with a pharmaceutically acceptable additives and/or excipients to produce an administrable form.

14. Method according to claim 13, comprising: providing approximately equimolar amounts of the corresponding base and acid, and combining the base and acid with the pharmaceutically acceptable additives and/or excipients.

15. Method for the treatment of tumor diseases, autoimmune diseases, cardiovascular diseases, infections, or viral diseases comprising administering to a patient a pharmaceutically effective amount of the pharmaceutical preparation of claim 1.

* * * * *

UNITED STATES PATENT AND TRADEMARK OFFICE
CERTIFICATE OF CORRECTION

PATENT NO. : 7,078,566 B2
APPLICATION NO. : 10/820121
DATED : July 18, 2006
INVENTOR(S) : Eberhard Amtmann It is certified that error appears in the above-identified patent and that said Letters Patent is hereby corrected as shown below:

Title Page, item [73] Assignee's name, delete "Biosphinks" and insert therefor
-- Biosphings --

Signed and Sealed this

Twenty-sixth Day of December, 2006

JON W. DUDAS
*Director of the United States Patent and Trademark Office*